US008202967B2

(12) United States Patent
Vaughn et al.

(10) Patent No.: US 8,202,967 B2
(45) Date of Patent: Jun. 19, 2012

(54) H5 PROTEINS, NUCLEIC ACID MOLECULES AND VECTORS ENCODING FOR THOSE, AND THEIR MEDICINAL USE

(75) Inventors: Eric Vaughn, Ames, IA (US); Paulino Carlos Gonzalez-Hernandez, Jalisco (MX); Juergen Däemmgen, Ochsenhausen (DE)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 11/923,326

(22) Filed: Oct. 24, 2007

(65) Prior Publication Data

US 2008/0193471 A1  Aug. 14, 2008

Related U.S. Application Data

(60) Provisional application No. 60/863,142, filed on Oct. 27, 2006.

(51) Int. Cl.
*C07K 1/00* (2006.01)
*A61K 39/00* (2006.01)
*A61K 39/145* (2006.01)

(52) U.S. Cl. .................. 530/350; 424/184.1; 424/206.1; 424/209.1

(58) Field of Classification Search .................. None
See application file for complete search history.

(56) References Cited

U.S. PATENT DOCUMENTS

| 4,552,758 | A | 11/1985 | Murphy et al. |
| 6,204,281 | B1 | 3/2001 | Webb et al. |
| 2004/0071733 | A1 | 4/2004 | Takaku et al. |
| 2004/0219208 | A1 | 11/2004 | Kawamura et al. |
| 2005/0042229 | A1 | 2/2005 | Yang et al. |
| 2007/0207168 | A1* | 9/2007 | Daemmgen et al. ....... 424/209.1 |

FOREIGN PATENT DOCUMENTS

| WO | 20050042229 A1 | 5/2005 |
| WO | 2005107797 A1 | 11/2005 |
| WO | 2007019094 A2 | 2/2007 |
| WO | 200753446 A2 | 5/2007 |
| WO | 2008052173 A2 | 5/2008 |

OTHER PUBLICATIONS

Philpott et al. J Virol. Jun. 1990;64(6):2941-7.*
Subbarao and Katz. Cell Mol Life Sci. Nov. 2000;57(12):1770-84. Review.*
Ioannou et al. J Virol. Sep. 2002;76(18):9002-10.*
The World Health Organizatin Global Influenza Program Surveillane Network. Evolution of H5N1 Avian Influenza Viruses in Asia. Emerging Infectious Diseases. 2005. 11(10): 1515-1521.*
Cinatl et al., "The threat of avian influenza A (H5N1). Part IV: development of vaccines". 2007, Medical Microbiology and Immunology, vol. 196, pp. 213-225.

Crawford et al., "Baculovirus-derived hemagglutinin vaccines protect against lethal influenza infections by avian H5 and H7 subtypes". 1999, Vaccine, vol. 17, pp. 2265-2274.
Hien et al., "Avian Influenza- A Challenge to Global Health Care Structures". 2004, New England Journal of Medicine, vol. 351, No. 23, pp. 2363-2365.
Hoffmann et al., "Role of specific hemagglutinin amino acids in the immunogenicity and protection of H5N1 influenza virus vaccines". Sep. 2005, Proceedings of the National Academy of Sciences, vol. 102, No. 36, pp. 12915-12920.
Iino et al., "Renoprotective Effect of Losartan in Comparison to Amlodipine in Patients with Chronic Kidney Disease and Hypertension-a Report of the Japanese Losartan Therapy Intended for the Global Renal Protection in Hypertensive Patients (JLIGHT) Study." 2004, Hypertension Research, vol. 27, No. 1, pp. 21-30.
International Search Report for PCT/US2006/041989 mailed on Jun. 29, 2007.
International Search Report PCT/US07/82699 mailed Aug. 20, 2008.
Karasin et al., "Isolation and Characterization of H4N6 Avian Influenza Viruses from Pigs with Pneumonia in Canada". Oct. 2000, Journal of Virology, vol. 74, No. 119, pp. 9322-9327.
Knossow et al., "Variation and infectivity neutralization in influenza". 2006, Immunology, vol. 119, pp. 1-7.
Lefebvre et al., "Angiotensin-converting enzyme inhibitors in the therapy of renal diseases". 2004, Journal of Veterinary Pharmacology and Therapeutics, vol. 27, No. 5, pp. 265-281.
Lim et al., "Mucosal vaccination against influenza: Protection of pigs immunized with inactivated virus of ether-split vaccine". 2001, Journal of Veterinary Research, vol. 48, No. 4, pp. 197-203.
Lipatov et al., "Influenza: Emergence and Control". Sep. 2004, Journal of Virology, vol. 78, No. 17, pp. 8951-8959.
Liu, et al. "Sequence comparison between the extracellular domain of M2 protein human and avian influenza A virus provides new information for bivalent influenza vaccine design". 2005, Microbes and Infection, vol. 7, pp. 171-177.
Lueschow, et al. "Protection of chickens from lethal avian influenza A virus infection by live-virus vaccination with infectious laryngotracheitis virus recombinants expressing the hemagglutinin (H5) gene". 2001, Vaccine, vol. 19, pp. 4249-4259.
Palese, Peter. "Influenza: old and new threats". Dec 2004, Nature Medicine Supplement, vol. 10, No. 12, pp. 582-587.
Philippa et al. "Highly pathogenic avian influenza (H7N7): Vaccination of zoo birds and transmission to non-poultry species". 2005, Vaccine, vol. 23, pp. 5743-5750.
Pushko, et al. "Influenza virus-like particles comprised of the HA NA and M1 proteins of H9N2 influenza virus induce protective immune responses in BALB/c mice". 2005, Vaccine, vol. 23, pp. 5751-5759.
Snively et al., "Chronic Kidney Disease: Prevention and Treatment of Common Complications". Nov. 2004, American Family Physician, vol. 70, No. 10, pp. 1921-1928.

(Continued)

*Primary Examiner* — Zachariah Lucas
*Assistant Examiner* — Michelle S Horning
(74) *Attorney, Agent, or Firm* — Michael P. Morris; Julie A. Scott

(57) ABSTRACT

The present invention relates to novel hemagglutinin H5 proteins, nucleic acids and vectors encoding for those as well as vaccines comprising any of such H5 proteins, nucleic acids or vectors encoding for those H5 proteins. Moreover, the present invention also relates to the medicinal use of any of such compositions in humans and animals.

13 Claims, No Drawings

OTHER PUBLICATIONS

Stephenson et al. "Confronting the avian influenza threat: vaccine development for a potential pandemic". Aug. 2004, The Lancet Infectious Diseases, vol. 4, pp. 499-509.

Stephenson et al. "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy". Apr. 2005, Journal of Infectious Diseases, vol. 191(8), pp. 1210-1215.

Stevens, et al., "Structure and Receptor Specificity of the Hemagglutinin from an H5N1 Influenza Virus". Apr. 2006, Science, vol. 312, pp. 404-410.

Suga et al., "Angiotensin II type 1 receptor blockade ameliorates tubulointerstitial injury induced by chronic potassium deficiency". 2002, Kidney International, vol. 61, pp. 951-958.

Thomson, "Vaccine Leader: Swine influenza virus . . . combination of pathogen avian influenza and human influenza". 2006, XP002437726, Database accession No. 2007-182327.

White et al., "Effects of the Angiotensin II Receptor Blockers Telmisartan Versus Valsartan on the Circadian Variation of Blood Pressure. Impact on the Early Morning Period". 2004, American Journal of Hypertension, vol. 17, pp. 347-353.

Genbank: AAT39066, Version AAT39066.1 GI:47834862, Jun. 6, 2004.

Genbank: AY575870, Version AY575870.1 GI:47834861, Jun. 6, 2004.

Guan et al.,"H5N1 influenza: A protean pandemic threat". Proceedings of the National Acadmey of Sciences, vol. 101, No. 21, May 2004, pp. 8156-8161.

Hungarian Search Report and Written Opinion for SG200902099-1 mailed on Feb. 3, 2011.

Nwe et al., "Expression of hemagglutinin protein from the avian influenza virus H5N1 in a baculovirus/insect cell system significantly enhanced by suspension culture". BMC Microbiology, vol. 6, No. 16, 2006, (http:llwww. biomedcentral.com/1471-2180/6/16).

Genbank: AAT39065, Version AAT39065.1 GI:47834860, Jun. 6, 2004.

Genbank: ABA55715, Version ABA55715.1 GI:76800616, Oct. 8, 2005.

Viseshakul et al., "The genome sequence analysis of H5N1 avian influenza A virus isolated from the outbreak among poultry populations in Thailand". Virology, vol. 328, 2003, pp169-176, 2004.

* cited by examiner

SEQUENCE LISTING

```
<160> NUMBER OF SEQ ID NOS: 6

<210> SEQ ID NO 1
<211> LENGTH: 551
<212> TYPE: PRT
<213> ORGANISM: avian influenza virus

<400> SEQUENCE: 1

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60
```

-continued

```
Pro Met Cys Asp Glu Phe Ile Asn Val Pro Glu Trp Ser Tyr Ile Val
 65                  70                  75                  80

Glu Lys Ala Asn Pro Ala Asn Asp Leu Cys Tyr Pro Gly Asn Phe Asn
                 85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Ser Ser Ser Phe Phe
130                 135                 140

Arg Asn Val Val Trp Leu Ile Lys Lys Asn Asp Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Val Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Lys Leu Val Leu Ala Thr Gly Leu Arg Asn Ser
305                 310                 315                 320

Pro Gln Arg Glu Arg Arg Lys Arg Gly Leu Phe Gly Ala Ile Ala
                325                 330                 335

Gly Phe Ile Glu Gly Gly Trp Gln Gly Met Val Asp Gly Trp Tyr Gly
            340                 345                 350

Tyr His His Ser Asn Glu Gln Gly Ser Gly Tyr Ala Ala Asp Lys Glu
        355                 360                 365

Ser Thr Gln Lys Ala Ile Asp Gly Val Thr Asn Lys Val Asn Ser Ile
370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
        435                 440                 445

Asp Lys Val Arg Leu Gln Leu Arg Asp Asn Ala Lys Glu Leu Gly Asn
450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495
```

```
Leu Lys Arg Glu Glu Ile Ser Gly Val Lys Leu Glu Ser Ile Gly Thr
            500                 505                 510

Tyr Gln Ile Leu Ser Ile Tyr Ser Thr Val Ala Ser Ser Leu Ala Leu
            515                 520                 525

Ala Ile Met Val Ala Gly Leu Ser Leu Trp Met Cys Ser Asn Gly Ser
        530                 535                 540

Leu Gln Cys Arg Ile Cys Ile
545                 550

<210> SEQ ID NO 2
<211> LENGTH: 567
<212> TYPE: PRT
<213> ORGANISM: duck influenza virus

<400> SEQUENCE: 2

Met Glu Lys Thr Val Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu L

```
Tyr Val Lys Ser Asn Lys Leu Val Leu Ala Thr Gly Leu Arg Asn Ser
                325                 330                 335

Pro Gln Arg Glu Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
        370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
        450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
        530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 3
<211> LENGTH: 568
<212> TYPE: PRT
<213> ORGANISM: duck influenza virus

<400> SEQUENCE: 3

Met Glu Lys Ile Val Leu Leu Phe Ala Ile Val Ser Leu Val Lys Ser
1

```
Lys Ile Gln Ile Ile Pro Lys Asn Ser Trp Ser Ser His Glu Ala Ser
            130                 135                 140
Leu Gly Val Ser Ser Ala Cys Pro Tyr Gln Gly Lys Ser Ser Phe Phe
145                 150                 155                 160
Arg Asn Val Val Trp Leu Ile Lys Lys Asn Asn Ala Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Arg Leu Tyr Gln
            195                 200                 205
Asn Pro Thr Thr Tyr Ile Ser Val Gly Thr Ser Thr Leu Asn Gln Arg
210                 215                 220
Leu Val Pro Lys Ile Ala Thr Arg Ser Lys Val Asn Gly Gln Asn Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Met Lys Ser Glu Leu Glu Tyr Gly
            275                 280                 285
Asn Cys Asn Thr Lys Cys Gln Thr Pro Met Gly Ala Ile Asn Ser Ser
290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
            355                 360                 365
Gly Tyr His His Ser Asn Glu Gln Gly Ser Gly Tyr Ala Ala Asp Lys
370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
            435                 440                 445
Glu Asn Glu Arg Thr Leu Asp Phe His Asp Ser Asn Val Lys Asn Leu
450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Arg Asn Gly Thr Tyr Asp Tyr Pro Gln Tyr Ser Glu Glu Ala
            500                 505                 510
Arg Leu Lys Arg Glu Glu Ile Ser Gly Val Lys Leu Glu Ser Ile Gly
            515                 520                 525
Thr Tyr Gln Ile Leu Ser Ile Tyr Ser Thr Val Ala Ser Ser Leu Ala
530                 535                 540
Leu Ala Ile Met Val Ala Gly Leu Ser Leu Trp Met Cys Ser Asn Gly
```

```
                545                 550                 555                 560
Ser Leu Gln Cys Arg Ile Cys Ile
                565

<210> SEQ ID NO 4
<211> LENGTH: 568
<212> TYPE: PRT
<213> ORGANISM: avinan influenza virus

<400> SEQUENCE: 4

Met Glu Lys Thr Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Asp His Glu Ala Ser
    130                 135                 140

Ser Gly Val Ser Ser Ala Cys Pro Tyr Gln Gly Ser Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Val Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
```

```
                    355                 360                 365
Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 5
<211> LENGTH: 263
<212> TYPE: PRT
<213> ORGANISM: Avian influenza virus

<400> SEQUENCE: 5

His Ala Asn Asn Trp Thr Glu Gln Val Asp Thr Ile Met Glu Lys Asn
1               5                   10                  15

Val Thr Val Thr His Ala Gln Asp Ile Leu Glu Lys Thr His Asn Gly
                20                  25                  30

Lys Leu Cys Asp Leu Asp Gly Val Lys Pro Leu Ile Leu Arg Asp Cys
            35                  40                  45

Ser Val Ala Gly Trp Leu Leu Gly Asn Pro Met Cys Asp Glu Phe Ile
    50                  55                  60

Asn Val Pro Glu Trp Ser Tyr Ile Val Glu Lys Ala Asn Pro Ala Asn
65                  70                  75                  80

Asp Leu Cys Tyr Pro Gly Asp Phe Asn Asp Tyr Glu Glu Leu Lys His
                85                  90                  95

Leu Leu Ser Arg Ile Asn His Phe Glu Lys Ile Gln Ile Ile Pro Lys
            100                 105                 110

Asn Ser Trp Ser Ser His Glu Ala Ser Leu Gly Val Ser Ser Ala Cys
    115                 120                 125

Pro Tyr Gln Gly Lys Ser Ser Phe Phe Arg Asn Val Val Trp Leu Ile
    130                 135                 140

Lys Lys Asn Asn Ala Tyr Pro Thr Ile Lys Arg Ser Tyr Asn Asn Thr
145                 150                 155                 160

Asn Gln Glu Asp Leu Leu Val Leu Trp Gly Ile His His Pro Asn Asp
```

```
                   165                 170                 175
Ala Ala Glu Gln Thr Arg Leu Tyr Gln Asn Pro Thr Thr Tyr Ile Ser
            180                 185                 190

Val Gly Thr Ser Thr Leu Asn Gln Arg Leu Val Pro Lys Ile Ala Thr
            195                 200                 205

Arg Ser Lys Val Asn Gly Gln Asn Gly Arg Met Glu Phe Phe Trp Thr
            210                 215                 220

Ile Leu Lys Pro Asn Asp Ala Ile Asn Phe Glu Ser Asn Gly Asn Phe
225                 230                 235                 240

Ile Ala Pro Glu Tyr Ala Tyr Lys Ile Val Lys Lys Gly Asp Ser Ala
            245                 250                 255

Ile Met Lys Ser Glu Leu Glu
            260

<210> SEQ ID NO 6
<211> LENGTH: 290
<212> TYPE: PRT
<213> ORGANISM: duck influenza virus

<400> SEQUENCE: 6

Gly Ser Ala Thr Met Glu Lys Thr Val Leu Leu Ala Ile Val Ser
1               5                   10                  15

Leu Val Lys Ser Asp Gln Ile Cys Ile Gly Tyr His Ala Asn Asn Ser
                20                  25                  30

Thr Glu Gln Val Asp Thr Ile Met Glu Lys Asn Val Thr Val Thr His
            35                  40                  45

Ala Gln Asp Ile Leu Glu Lys Thr His Asn Gly Lys Leu Cys Asp Leu
50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Ala Asn Asp Leu Cys Tyr Pro
            100                 105                 110

Gly Asn Phe Asn Asp Tyr Glu Glu Leu Lys His Leu Leu Ser Arg Ile
            115                 120                 125

Asn His Phe Glu Lys Ile Gln Ile Ile Pro Lys Ser Ser Trp Ser Asp
130                 135                 140

His Glu Ala Ser Ser Gly Val Ser Ser Ala Cys Pro Tyr Gln Gly Ser
145                 150                 155                 160

Ser Ser Phe Phe Arg Asn Val Val Trp Leu Ile Lys Lys Asn Asp Ala
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
            195                 200                 205

Arg Leu Tyr Gln Asn Pro Thr Thr Tyr Ile Ser Val Gly Thr Ser Thr
            210                 215                 220

Leu Asn Gln Arg Leu Val Pro Lys Ile Ala Thr Arg Ser Lys Val Asn
225                 230                 235                 240

Gly Gln Ser Gly Arg Met Asp Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270
```

```
Ala Tyr Lys Ile Val Lys Lys Gly Asp Ser Ala Ile Met Lys Ser Glu
        275                 280                 285
Val Glu
    290
```

H5 PROTEINS, NUCLEIC ACID MOLECULES AND VECTORS ENCODING FOR THOSE, AND THEIR MEDICINAL USE

RELATED APPLICATIONS

This application claims the priority benefit of U.S. Provisional Patent Application Ser. No. 60/863,142, filed on Oct. 27, 2006, the teachings and content of which are hereby incorporated by reference.

FIELD OF THE INVENTION

The present invention relates to the field of medicine, preferably to the field of infectious diseases. In particular the present invention relates to influenza proteins, nucleic acid molecules and vectors encoding those proteins, and vaccines. Most particularly, the present invention relates to the use of any of such proteins, nucleic acid molecules, vectors or vaccines for the treatment and prevention of influenza infections, furthermore for the prevention of intra- and inter-species transmission of influenza virus.

BACKGROUND OF THE INVENTION

Influenza infection remains an important infection in animals and humans. Influenza is caused by viruses that undergo continuous antigenic changes/modifications and that possess an animal reservoir. Thus new epidemics and pandemics may occur in the future, and eradication of the disease will be difficult to achieve, Influenza viruses are well known in the art and described more in detail for example by P. Palese, *Nature Medicine*, vol. 10, no. 12, pp. S 82 to S 86 of December 2004, with further references. Briefly, the genome of the influenza A virus consists of eight single-stranded segments, and the viral particles has two major glycoproteins on its surface: hemagglutinin (H) and neuraminidase (N). With at least 16 different hemagglutinin (H1 to H16) and 9 different neuraminidase (N1 to N9) subtypes, there is a considerable antigenic variation among influenza viruses.

Influenza virus of type H5N1 Fowl Plague virus has been demonstrated to infect poultry, pigs and man. The viruses can also be transmitted directly from avian species to humans (Claas et al., *Lancet* 1998; 351: 47; Suarez et al., *J. Virol.* 1998; 72: 6678; Subbarao et al., *Science* 1998, 279: 393; Shortridge, *Vaccine* 1999, 17 (Suppl 1): S26-S29). Mortality in known human clinical cases approaches about 50%.

Over the last century pigs have been an important vector for influenza pandemics. Pigs, camels, and seals, preferably pigs, can serve as a 'mixing chamber' for avian influenza viruses, and therefore represent a potential risk factor for overcoming the species hurdles from poultry, the naturally reservoir of influenza viruses, to mammals. This normally occurs by double infections of the susceptible animals, e.g. pig, with both, an established mammalian (porcine), as well as an avian influenza virus. This double infection may create new recombinant viruses that may be the cause of human or porcine pandemics. Recent evidence would, however, indicate that a recombination of current avian H5 strains with mammalian influenza viruses will not result in highly virulent recombinants. On the other hand, avian influenza virus can infect pigs and by spontaneous mutations can become adapted to pigs. The critical hurdle will be overcome as soon as the virus can cause horizontal infections within a pig (or other mammalian) population.

Yet, a major part of Southeast Asian pigs have been infected with avian (H5) influenza virus strains originating from neighbouring poultry husbandry. As those infections have so far been sub-clinical, they can only be diagnosed by laboratory methods and thus are frequently overlooked. There is a high risk that those sub-clinically-infected pigs will serve as an opportunity for the virus to adapt to the mammalian system, spread within the porcine population, and also infect human beings.

Current influenza vaccines include a subunit vaccine (Babai et al., *Vaccine* 1999, 17(9-10):1223-1238, Crawford et al., *Vaccine* 1999, 17(18):2265-2274: Johansson et al., *Vaccine* 1999, 17(1516):2073-2080) attenuated vaccine (Horimoto et al., *Vaccine* 2004, 22(17-18):2244-2247), DNA vaccine (Watabe et al., *Vaccine* 2001, 19(31):4434-4444) and inactivated influenza vaccine (Cao et al., *Vaccine* 1992, 10(4):238-243), with the latter being the most widely used on a commercial scale (Lipatov et al., *J Virol* 2004, 78(17):8951-8959).

Subunit vaccines, recombinant hemagglutinin and neuraminidase (Babai et al., *Vaccine* 1999, 17(9-10):1223-1238, Crawford et al., *Vaccine* 1999, 17(18):2265-2274; Johansson et al., *Vaccine* 1999, 17(1516):2073-2080) may be an attractive alternative to the inactivated vaccine, although none are currently in use as commercial vaccines. The preparation of such vaccines is obviously safer than for an inactivated vaccine. Moreover, subunit vaccines do not generate antibody responses to internal influenza viral proteins and thus allow distinction between vaccinated and infected animals (Crawford et al., *Vaccine* 1999, 17(18) 2265-2274).

Hemagglutinin protein is the receptor-binding and membrane fusion glycoprotein of influenza virus and the target for infectivity-neutralizing antibodies. The entire hemagglutinin protein (HA) from the H5N1 is composed of 568 amino acids, with a molecular weight of 56 kDa. The HA molecule consists of HA1 and HA2 subunits, with the HA1 subunit mediating initial contact with the cell membrane and HA2 being responsible for membrane fusion (Chizmadzhev, *Bioelectrochemistry* 2004, 63(1-2):129-136).

Baculovirus/insect cell systems have been used to express hemagglutinin genes isolated from avian influenza subtypes (Babai et al., *Vaccine* 1999, 17(9-10): 1223-1238, Crawford et al., *Vaccine* 1999, 17(18):2265-2274; Johansson et al., *Vaccine* 1999, 17(15-16):2073-2080); Nwe et al., *BMC Mircobiology* 2006, 6(16):doi:10.1186/1471-2180-6-16). However, the those recombinant proteins seems not to be protective in any case, or only less effective at least for some species (Treanor et al., Vaccine 2001, 19: 1732-1737).

Thus, there is a need to increase availability of improved vaccines and new vaccination approaches to provide better approaches to control influenza infections and to have a positive impact on disease load.

DESCRIPTION OF THE INVENTION

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations; reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

Influenza Proteins and Nucleic Acid Molecules Coding for Those

The present invention relates to a H5 protein of influenza virus, wherein the H5 protein having the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted. Preferably, such H5 protein and any further H5 protein according to the invention is an isolated H5 protein. It has been surprisingly found, that H5 proteins, having the modifications described above, are highly antigenic as compared to H5 proteins that do not have the corresponding amino acids at position 223 and 3281329.

The term "hemagglutinin 5 (H5)" or "H5 of avian influenza virus" or H5 protein" as used herein means, but is not limited to any naturally occurring H5 protein and any modified forms of H5 protein, including any deletion, substitution and/or insertion mutant of H5 protein, wherein those H5 proteins having the amino acid 223N and the modification 328K+.

The numbering of the amino acid positions of the H5 protein as used herein refers to the amino acid position as exemplarily given in SEQ ID NO:1. SEQ ID NO:1 represents the amino sequence of the hemagglutinin of strain duck/China/E319-2/03 but lacking the amino terminal signal peptide. In other words, if reference is made to the amino acid at position 223 (amino acid 223), the amino acid residue is meant which corresponds to amino acid 223 of SEQ ID NO:1. However, this does not mean that the H5 proteins according to the invention have the identical amino acid sequence with SEQ ID NO:1. It only says, that the corresponding amino acids of the H5 proteins according to the inventions code for the amino acid residue, as explicitly mentioned. In the current case, amino acid 223 would be Serine (S). The terms "223N", or "155N" exemplarily mean, that the amino acid at positions 223 and 155, respectively—numbering according to the amino acid positions of SEQ ID NO:1—, that shall code for the amino acid Asparagine (N). In other words, if reference is made to "H5 protein having the amino acid 223N", a H5 amino acid molecule that normally codes for Serine at amino acid position 223—numbering according to the amino acid positions of SEQ ID NO:1—that amino acid shall be substituted by an Asparagine (N). The term "328K+" or "modification 328K+" means, that at amino acid position 328 of H5 protein—numbering according to the amino acid positions of SEQ ID NO:1—, a second Lysine (K+) is inserted. In cases were amino acids sequences at positions 328 and 329 naturally codes for Lysine-Lysine, no further Lysine (K) shall be inserted. However, most of the known H5 sequences code at amino acid positions 328 and 329 for Lysine-Arginine. In any such cases, the term 328K+ modification means, that a second Lysine (K) shall be inserted between Lysine at position 328 and Arginine at position 329. The modified sequence would read then Lysine-Lysine-Arginine (KKR).

Thus, the present invention relates to the H5 protein and any modified forms of H5 protein, including any deletion, substitution and/or insertion mutant of H5 protein, wherein those H5 proteins having the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted. It is self-explanatory, that any of the H5 proteins as provided herewith are antigenic, which mean they show antigenic properties in an standard hemagglutinin inhibition assay for influenza viruses.

According to a further embodiment, the present invention also relates to any part of the H5 protein, which means any peptide-fragment which shows antigenic properties in an standard hemagglutinin inhibition assay, having at least the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted.

A H5 protein shows antigenic properties if it inhibits hemagglutination in a standard hemagglutinin inhibition assay, for examples as described in Example 2. Normally said antigenic part of H5 protein comprises 200, 180, 160, 150, 140, 130, 120, 110 or most preferably 105 contiguous amino acids of the amino acid sequence that codes for the H5 protein as mentioned above, modified or non-modified, which shows antigenic properties in an standard hemagglutinin inhibition assay as described in Example 2. A standard hemagglutinin inhibition assay for example is also described in Stephenson et al., Virus Research vol. 103, pp. 91-95 (2004) with further references. However, the HI assay as described in Example 2 shall be understood to be the relevant reference assay in connection with all aspects of the invention as described herein:

Briefly, HI assay was performed to detect the presence of HA-specific antibodies. A heterologous H5N2 virus, A/chicken/Mexico/232/94, was used at a concentration of four hemagglutinating units [4 HA units] in the HI assay. In U-bottomed microtiter plates serial two-fold serum dilutions in PBS were subsequently mixed with equal volumes (25 µL) containing 4 HA units of virus, and incubated at room temperature (about 25° C.) for 30 min. Chicken red blood cells, at a concentration of 0.5% in PBS, were added to the serum-virus containing wells and incubated for 40 min at room temperature. The HI titers were determined as reciprocals of the highest serum dilutions in which inhibition of hemagglutination was observed.

Of note, Haesebrouck and Pensaert (1986) found "that there may exist a correlation between the HI titers against the challenge virus and protection from challenge". Haesebrouck and Pensaert (1986) also determined that pigs with HI titers of $\geq 40$ were "completely resistant to challenge and no replication of the virus occurred in the respiratory tract at challenge". Thus, the development of HI titers $\geq 40$ in the vaccinated swine would correlate to protection. (F. Haesebrouck and M. B. Pensaert, 1986). Effect of intratracheal challenge of fattening pigs previously immunized with an inactivated influenza H1N1 vaccine (*Veterinary Microbiology*, 11 (1986) 239-249. It has to assume that equivalent or at least nearly equivalent H5 HI titers will also result in a complete immune protection of swine against avian influenza virus. Lower titers, at least result in a seroconversion of the vaccinated animals and result in partial immune protection of those animals, which also can dramatically reduce the risk of a pandemics.

Moreover, an antigenic pad of the H5 protein according to the invention includes, but is not limited to deletion mutants of H5 protein, which comprises:
i. at least 35, 30, 25, 20, 18, 15, 13, 10, 9, or most preferably 8 contiguous amino acids of the amino acid sequence that surrounds and includes the amino acid 223N; and
ii. at least 35, 30, 25, 20, 18, 15, 13, 10, 9, or most preferably 8 contiguous amino acids of the amino acid sequence that surrounds and includes the amino acid modification 328K+, and
iii. wherein any of such antigenic part of H5 protein shows hemagglutinin inhibition in a standard hemagglutinin inhibition assay as described in Example 2.

Preferably, those surrounding amino acids of amino acid 223N and/or 328K+ are encoded by SEQ ID NO:1 or SEQ ID NO:4.

Furthermore preferred H5 proteins according to the invention are:
i. any of those mentioned above having the amino acid 223N and the modification 328K+;
ii. any of those mentioned above having the amino acid 94N/223N and the modification 328K+;
iii. any H5 protein of avian origin having the amino acid 223N, and the modification 328K+, wherein avian origin means that the H5 sequence derived form a virus isolate that was originally isolated from a poultry infected with avian influenza virus type 5; or
iv, any H5 protein of avian origin having the amino acids 94N1223N and the modification 328K+, wherein avian origin means that the H5 sequence derived from a virus isolate that was originally isolated from poultry infected with avian influenza virus type 5; or
v. any H5 protein of avian origin having the amino acids 155N/223N and the modification 328K+, wherein avian origin means that the H5 sequence derived from a virus isolate that was originally isolated from poultry infected with avian influenza virus type 5; or
vi. any H5 protein of avian origin having the amino acid 120N/155N/223N and the modification 328K+, wherein avian origin means that the H5 sequence derived from a virus isolate that was originally isolated from poultry infected with avian influenza virus type 5; or
vii. any H5 protein having the modifications 94N/223N and the modification 328K+; or
viii. any H5 protein having the modifications 94N/155N/223N and the modification 328K+; or;
ix. any H5 protein having the modifications 94N/120N/455N/223N and the modification 328K+; or
x. any H5 protein having the modifications 223N, the modification 328K+, and one or more of the following amino acid clusters selected from the group consisting of;
a. aa 93-95: GNF
b. aa 123-125; SDH
c. aa 128-130: SSG
d. aa 139-141: GSS
e. aa 226-228: MDF
f. aa 268-270: EVE
g. aa 309-311: NKL; or
xi. any H5 protein having the amino acid 223N, and the modification 328K+, and one or more of the following amino acid clusters selected from the group consisting of:
a. aa 93-95: GNF
b. aa 128-130: SSG
c. aa 139-141: GSS; or
xii. any H5 protein having the amino acid sequence of SEQ ID NO:4.

Furthermore preferred H5 proteins as provided herewith include the H5 proteins as described by Hoffmann et al, *PNAS*, vol. 106, no. 36 pp. 12915-12920 of Sep. 6, 2005, wherein that H5 proteins includes one or more of the modifications as described above, at least the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted. The disclosure of this reference shall be entirely included herein by reference.

Furthermore preferred H5 proteins as provided herewith include H5 proteins which comprise a peptide that comprises the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted, and:
i. the amino acid sequences of SEQ ID N1, SEQ ID NO:2, SEQ ID NO:3; SEQ ID NO:4; SEQ ID NO:5 or SEQ ID NO:6 or;
ii. any peptide that has at least 85% sequence homology, more preferably at least about 90% sequence homology, still more preferably at least about 95% sequence homology, even more preferably at least about 97% sequence homology, still even more preferably at least about 98% sequence homology, and even more preferably at least about 99% sequence homology to the polypeptide of i) that comprises hemagglutinin inhibition in a standard hemagglutinin inhibition as described above; or
iii. any antigenic pad of the polypeptides of i) or ii) comprising at least 35, 30, 25, 20, 18, 15, 13, 10, 9, or most preferably 8 contiguous amino acids of any of peptides of i) or ii).
iv. any peptides of i), ii) or iii) having the amino acids 36T, 36K, 83A, 83T, 83D, 86A, 86V, 120N, 120S, 155N, 155S, 156A, 156T, 189R, 189K, 212K, 212R, 212E, 223N, 223N, or 120N1155N.
v. any peptide of i), ii), iii) or iv) having one or more of the following amino acid clusters selected from the group consisting of,
a. aa 93-95: GNF
b. aa 123-125: SDH
c. aa 128-130: SSG
d. aa 139-141: GSS
e. aa 226-228: MOF
f. aa 268-270: EVE
g. aa 309-311: NKL; or
vi. any peptide of i), ii) iii) or iv) having one or more of the following amino acid clusters selected from the group consisting of,
a. aa 93-95: GNF
b. aa 128-130: SSG
c. aa 139-141: GSS.

"Sequence homology", as used herein, refers to a method of determining the relatedness of two sequences. To determine sequence homology, two or more sequences are optimally aligned, and gaps are introduced if necessary. In contrast to sequence identity, conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides. Upon such alignment, sequence homology is ascertained on a position-by-position basis, e.g., the sequences are "homolog" at a particular position if at that position, the nucleotides or amino acid residues are identical. The total number of such position identities is then divided by the total number of nucleotides or amino acid residues in the reference sequence to give % sequence homology. Sequence homology can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993): Computer Analysis of Sequence Data, Part I, Griffin, A. M., and Griffin, H. G., eds., Humana Press, New Jersey (1994); Sequence Analysis in Molecular Biology, von Heinge, G., Academic Press (1987): Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence homology are designed to give the largest match between the sequences tested. Methods to determine sequence homology are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F, et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence homology between the given and reference sequences.

Furthermore preferred H5 proteins include H5 proteins which comprise the 328K+ modification as mentioned above, and the amino acid sequence provided in TABLE 1, or any immunogenic part thereof:

TABLE 1

H5 antigens

| Sequence name | Basic-sequence | Amino acid positions[#] | | | | | | | | | |
|---|---|---|---|---|---|---|---|---|---|---|---|
| | | 36 | 83 | 86 | 120 | 155 | 156 | 189 | 212 | 223 | 263 |
| 223N/328K+ | any HA H5 | — | — | — | — | — | — | — | — | N | — |
| 36T/223N/328K+ | any HA H5 | T | — | — | — | — | — | — | — | N | — |
| 36K/223N/328k+ | any HA H5 | K | — | — | — | — | — | — | — | N | — |
| 83A/223N/328k+ | any HA H5 | — | A | — | — | — | — | — | — | N | — |
| 83T/223N/328k+ | any HA H5 | — | T | — | — | — | — | — | — | N | — |
| 83D/223N/328k+ | any HA H5 | — | D | — | — | — | — | — | — | N | — |
| 86A/223N/328k+ | any HA H5 | — | — | A | — | — | — | — | — | N | — |
| 86V/223N/328k+ | any HA H5 | — | — | V | — | — | — | — | — | N | — |
| 120N/223N/328k+ | any HA H5 | — | — | — | N | — | — | — | — | N | — |
| 120S/223N/328k+ | any HA H5 | — | — | — | S | — | — | — | — | N | — |
| 155N/223N/328k+ | any HA H5 | — | — | — | — | N | — | — | — | N | — |
| 155S/223N/328k+ | any HA H5 | — | — | — | — | S | — | — | — | N | — |
| 156A/223N/328k+ | any HA H5 | — | — | — | — | — | A | — | — | N | — |
| 156T/223N/328k+ | any HA H5 | — | — | — | — | — | T | — | — | N | — |
| 189R/223N/328k+ | any HA H5 | — | — | — | — | — | — | R | — | N | — |
| 189K/223N/328k+ | any HA H5 | — | — | — | — | — | — | K | — | N | — |
| 212K/223N/328k+ | any HA H5 | — | — | — | — | — | — | — | K | N | — |
| 212R/223N/328k+ | any HA H5 | — | — | — | — | — | — | — | R | N | — |
| 212E/223N/328k+ | any HA H5 | — | — | — | — | — | — | — | E | N | — |
| 223N/263A/328k+ | any HA H5 | — | — | — | — | — | — | — | — | N | A |
| 223N/263T/328k+ | any HA H5 | — | — | — | — | — | — | — | — | N | T |
| 120N/155N/223N/328k+ | any HA H5 | — | — | — | N | N | — | — | — | N | — |
| A/duck/China/E319-2/03/328k+ | AAR99628 | T | A | A | S | D | A | R | K | N | A |
| A/duck/China/E319-2/03_223N/328k+ | AAR99628 | T | A | A | S | D | A | R | K | N | A |
| A/duck/China/E319-2/03_120N/223N/328k+ | AAR99628 | T | A | A | N | D | A | R | K | N | A |
| A/duck/China/E319-2/03_155N/223N/328k+ | AAR99628 | T | A | A | S | N | A | R | K | N | A |
| A/duck/China/E319-2/03_120N/155N/223N/328k+ | AAR99628 | T | A | A | S | N | N | R | K | N | A |
| HA/HK/213/03/328k+ | AY518362 | T | A | A | N | N | A | R | K | N | A |
| HA/Vietnam/1203/04 | | K | T | V | S | S | T | K | R | N | T |
| HA/Vietnam/1203/04_223N/328k+ | | K | T | V | S | S | T | K | R | N | T |
| HA//Vietnam/3046/04_223N/328k+ | | T | A | V | S | S | T | K | R | N | T |
| HA/Vietnam/3062/04_223N/328k+ | | T | A | V | S | S | T | K | R | N | T |
| HA/chicken/Vietnam/39/04_223N/328k+ | | T | A | V | S | S | T | K | R | N | T |

TABLE 1-continued

H5 antigens

| Sequence name | Basic-sequence | Amino acid positions[#] | | | | | | | | | |
|---|---|---|---|---|---|---|---|---|---|---|---|
| | | 36 | 83 | 86 | 120 | 155 | 156 | 189 | 212 | 223 | 263 |
| HA/falcon/HK-D0028/04_223N/328k+ | | T | A | A | S | S | A | K | E | N | A |
| HA/duck/Singapore/3/97_223N/328k+ | | T | D | V | S | N | A | K | E | N | A |
| HA/HK/156/97/328k+ | | T | A | A | S | S | A | K | E | N | T |

[#]the amino acid positions given in TABLE 1 refers to the positions as exemplarily defined in SEQ ID NO: 1. In other words amino acid 223 of TABLE 1 refers to the amino acid 223 of the sequence of SEQ ID NO: 1.
— means that the amino acids at this positions are variable as compared to the reference sequence Furthermore, the present invention also relates to H5 proteins having at least the amino acid 223N and the modification 328K+, wherein numbering of the amino acid positions of the H5 protein refers to the amino acid position as exemplarily given in SEQ SD NO:1 and wherein the modification 328K+ means that at amino acid position 328 of H5 protein a second Lysine (K+) is inserted, and comprises:

i. a peptide having the sequences of NCBI Accession No. AAT65209, CAJ32556, ABC47656, CAF21874, CAF21870, AAC58998, AAC58997, AAC58996. AAC58994, AAC58993, AAC58992, AAC58991, AAC58990, AAC58995, AAS45134, AAN17270, AAN17269, AAN17268, AAN17267, AAN7266, AAN17265, AAN17264, AAN17263, AAN17262, AAN17261, AAN17260, AAN17259, AAN17257, AAN17256, AAN17255, AAN17254, AAA43083, AAA43082, AAB19079, BAE48696, BAE48693, BAE48696, BAE48695, BAE48694, BAE48692, BAE48691, BAE48690, BAE48689, BAE48688, BAE48687, BAE48686, BAE48685, BAE48684, BAE48683, AAC58999, ABC72082, AAV91149, AAP71993, AAP71992, AAP71991, AAP71990, AAP71989, AAP72011, AAP72010, AAP72009, AAP72008, AAP72007, AAP72006, AAP72005, AAP72004, AAP72003, AAP72002, AAP72001, AAP72000, AAP71999, AAP71998, AAP71997, AAP71996, AAP71995, AAP71994, AAF99718, ABF58847, AAG38534, AAC32102, AAC32099, AAL75847, AAC32101, AAC32098, AAC32088, AAC32078, AAR99628, AAC32100, AAM49555, AAL75843, AAL75839, AAD13573, AAD13568, AAF04720, AAF04719, AAC34263, AAR16155, AAD13574, AAD13570, AAD13575, AAD13572, AAD13569, AAD13567, AAD13566, AAK57506, AAG01225, AAG01215, AAG01205, AAG01195, or ABD83813 modified in a manner described above, which means that those sequences include the above-mentioned modifications 223N and 328 K+ which are not part of the wild-type sequences; or ii. any peptide that has at least 85% sequence homology, more preferably at least about 90% sequence homology, still more preferably at least about 95% sequence homology, even more preferably at least about 97% sequence homology, still even more preferably at least about 98% sequence homology, and even more preferably at least about 99% sequence homology to the polypeptide of i) and that show hemagglutinin inhibition in a standard hemagglutinin inhibition as described above;

iii. any of the peptides of 7) or ii) having the amino acids 36T, 36K, 83A, 83T, 83D, 86A, 86V, 120N, 120S, 155N, 155S, 156A, 156T, 189R, 189K, 212K, 212R, 212E, 263A, 263T, or 120N/155N; or iv. any of such peptides of i), ii), or iii) having one or more of the following amino acid clusters selected from the group consisting of,
a. aa 93-95: GNF
b. aa 123-125 SDH
c. aa 128-130: SSG
d. aa 139-141: GSS
e. aa 226-228: MDF
f. aa 268-270: EVE
g. aa 309-311: NKL; or v. any peptide of i), ii) iii) or iv) having one or more of the following amino acid clusters selected from the group consisting of:
a. aa 93-95: GNF
b. aa 128-130: SSG
c. aa 139-141: GSS According to a further embodiment, the present invention also relates to nucleic acid molecules, which code for any of the H5 proteins as described supra. Preferably, those nucleic acid molecules are RNA, DNA or copy (c)DNA molecules. Thus, the present invention relates to a nucleic acid molecule, preferably a cDNA molecule coding for a H5 protein or any modified forms of H5 protein, including any deletion, substitution and/or insertion mutant of H5 protein, wherein those H5 proteins having the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted.

According to a further embodiment, the present invention also relates to a nucleic acid molecule, preferably a cDNA molecule coding for any part of the H5 protein, which means encoding for any peptide-fragment which shows antigenic properties in an standard hemagglutinin inhibition assay as described supra, and having at least the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted. Normally such nucleic acid molecules, which code for an antigenic part of H5 protein, comprise 600, 540, 480, 450, 420, 390, 360, 330 or most preferably 315 contiguous nucleotides of the nucleotide sequence that codes for the H5 protein as mentioned above, modified or non-modified, and which shows antigenic properties in an standard hemagglutinin inhibition assay as described herein.

Further embodiments of antigenic parts of the H5 protein are described supra. It is in the common knowledge of a person skilled in the art to construct any such nucleic acid molecules, preferably cDNA molecules which codes for the antigenic part of the H5 protein as described supra. This also include but is not limited to the construction of nucleic acid molecules, preferably of cDNA molecules, which codes for antigenic parts of the H5 protein as mentioned above including deletion mutants of H5 protein, which comprises:
   i. at least 105, 90, 75, 60, 48, 45, 39, 30, 27, or most preferably 24 contiguous amino nucleotides of the nucleotide sequence that surrounds and includes the coding sequence that codes for amino acid 223N; and
   ii. at least 105, 90, 75, 60, 48, 45, 39, 30, 27, or most preferably 24 contiguous amino nucleotides of the nucleotide sequence that surrounds and includes the coding sequence that codes for modification 328K+, and
   iii. wherein any of such antigenic part of H5 protein show hemagglutinin inhibition in a standard hemagglutinin inhibition assay as described in Example 2.

Preferably, those surrounding nucleotides of the nucleotides, which code for amino acids 223N and/or 328K+, coding for SEQ ID NO:1 or SEQ ID NO:4.

Furthermore preferred nucleic acid molecules encoding for the H5 protein according to the invention are:
i. any of those mentioned supra encoding for the amino acid 223N and the modification 328K+;
ii. any of those mentioned supra encoding for the amino acid 94N/223N and the modification 328K+;
iii. any nucleic acid molecules of avian origin encoding for the amino acid 223N, and the modification 328K+, wherein avian origin means that the H5 sequence derived from a virus isolate that was originally isolated from poultry infected with avian influenza virus type 5, or
iv. any nucleic acid molecules of avian origin encoding for the amino acids 94N/223N and the modification 328K+, wherein avian origin means that the H5 sequence derived from a virus isolate that was originally isolated from poultry Infected with avian influenza virus type 5; or.
v. any nucleic acid molecules of avian origin encoding for the amino acids 155N/223N and the modification 328K+, wherein avian origin means that the H5 sequence derived from a virus isolate that was originally isolated from poultry infected with avian influenza virus type 5; or
vi. any nucleic acid molecule encoding for H5 protein of avian origin having the amino acid 120N/155N/223N and the modification 328K+, wherein avian origin means that the H6 sequence derived from a virus isolate that was originally isolated from poultry infected with avian influenza virus type 5; or
vii. any nucleic acid molecule encoding for H5 protein having the modifications 94N/223N and the modification 328K+; or
viii. any nucleic acid molecule encoding for H5 protein having the modifications 94N/155N/223N and the modification 328K+; or;
ix. any nucleic acid molecule encoding for H5 protein having the modifications 94N/120N/155N/223N and the modification 328K+; or
x. any nucleic acid molecule encoding for H5 protein having the modifications 223N, the modification 328K+, and one or more of the following amino acid clusters selected from the group consisting of:
a. aa 93-95: GNF
b. aa 123-125: SDH
c. aa 128-130: SSG
d. aa 139-141: GSS
e. aa 226-228: MDF
f. aa 268-270: EVE
g. aa 309-311: NKL; or xi. any nucleic acid molecule encoding for H5 protein having the amino acid 223N, the modification 328K+, and one or more of the following amino acid clusters selected from the group consisting of:
a. aa 93-95: GNF
b. aa 128-130: SSG
c. aa 139-141: GSS; or
xii. any nucleic acid molecule encoding for H5 protein having the amino acid sequence of SEQ ID NO:4.

Furthermore preferred H5 proteins as provided herewith include the H5 proteins as described by Hoffmann et al, *PNAS, vol.* 106 no. 36, pp. 12915-12920 of Sep. 6, 2005, wherein that H5 proteins includes one or more of the modifications as described above, at least the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted. The disclosure of this reference shall be entirely included herein by reference. Thus according to a further embodiments, the present invention also relates to any nucleic acid molecule, preferably a cDNA molecule coding for any of such proteins described by Hoffmann et al, *PNAS*, vol. 106, no. 36, pp. 12915-12920 of Sep. 6; 2005, wherein that H5 proteins includes 110 one or more of the modifications as described above, at least the amino acid 223N and the modification 328K+, wherein numbering of the amino acid positions of the H5 protein refers to the amino acid position as exemplary given in SEQ ID NO:1 and wherein the modification 328K+ means that at amino acid position 328 of H5 protein a second Lysine (K+) is inserted.

Methods, of how to introduce any of the above-mentioned modifications within the nucleotide sequence, including the encoding sequence of the H5 protein of an influenza virus, are well known in the art. The genomic sequence of the entire influenza virus can be modified according to the invention, for example according to the methods described in U.S. Pat. No. 6,951,754, with further references.

Furthermore, there may be employed conventional molecular biology, microbiology, and recombinant DNA techniques within the skill of the art to modify a nucleic acid sequence coding for an antigen as described herein. Such techniques are explained fully in the literature. See, e.g., Sambrook et al., *Molecular Cloning: A Laboratory Manual, Second Edition* (1989) Cold Spring Harbor Laboratory Press, Cold Spring Harbor, N.Y.; *DNA Cloning: A Practical Approach, Volumes I and II* (D. N. Glover ed. 1985), *Oligonucleotide Synthesis* (M. J. Gait ed. 1984.); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols In Molecular Biology*, John Wiley & Sons, Inc. 1994).

According to a further embodiment, the present invention also relates to a vector that comprises any of such nucleic acid molecules as described supra. In other words, the present invention relates to a vector, that includes the coding sequence of any such H5 protein, or part thereof as described supra. Preferably, said vector is an expression vector, which allows the expression of any such H5 protein or part thereof as described supra. Vectors according to the invention are those which are suitable for the transfection or infection of bacterial, yeast or animal cells, in vitro or in vivo.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 51762,938, 5,770,212, 5,942,235,382, 425, PCT publications WO 94/16716, WO 96/39491, WO 95/30018, Paoletti, "Applications of pox virus vectors to vaccination: An update, "PNAS USA 93: 11349-11353, October 1996, Moss, "Genetically engineered poxviruses for recombinant gene expression, vaccination, and safety," PNAS USA 93: 11341-11348, October 1996, Smith et al., U.S. Pat. No. 4,745,051, (recombinant baculovirus), Richardson, C. D. (Editor), Methods in Molecular Biology 39, "Baculovirus Expression Protocols" (1995 Humana Press Inc.), Smith et al., "Production of Human Beta Interferon in Insect Cells Infected with a Baculovirus Expression Vectors", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 399-406; EPA0 370 573, U.S. application No. 920,197, filed Oct. 16, 1986, EP Patent publication No. 265785, U.S. Pat. No. 4,769,331 (recombinant herpesvirus), Roizman, "The function of herpes simplex virus genes' A primer for genetic engineering of novel vectors," PNAS USA 93:11307-11312, October 1996, Andreansky et al., "The application of genetically engineered herpes simplex viruses to the treatment of experimental brain tumors," PNAS USA 93: 11313-11318. October 1996, Robertson et al. "Epstein-Barr virus vectors for gene delivery to B lymphocytes", PNAS USA 93: 11334-11340, October 1996, Frolov et al., "Alphavirus-based expression vectors: Strategies and applications," PNAS USA 93: 11371-11377, October 1996, Kitson et al., J. Virol. 65, 3068-3075, 1991; U.S. Pat. Nos. 5,591,439, 5,552,143, WO 98/00166, allowed U.S. application Ser. Nos. 08/675,556, and 08/675,566 both filed Jul. 3, 1996 (recombinant adenovirus), Grunhaus et al., 1992, "Adenovirus as cloning vectors." Seminars in Virology (Vol. 3) p. 237-52, 1993, Ballay et al. EMBO Journal, vol. 4, p. 3861-65, Graham, Tibtech 8, 85-87, April, 1990, Prevec et al., J. Gen Virol. 70, 42434, PCT WO 91/11525. Felgner et al. (1994), J. Biol. Chem. 269, 2550-2561, Science, 259: 1745-49, 1993 and McClements et al., "immunization with DNA vaccines encoding glycoprotein D or glycoprotein B, alone or in combination, induces protective immunity in animal models of herpes simplex virus-2 disease", PNAS USA 93: 11414-11420, October 1996, and U.S. Pat. Nos. 5,591,639, 5,589,466, and 5,580,859, as well as WO 90/11092, WO93/19183, WO94/21797, WO95/11307, WO95/20660, Tang et al., Nature and Furth et al. Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel), WO 90/01543: Robinson et al., seminars in Immunology vol. 9, pp. 271-283 (1997), (DNA vector systems); Szoka et al., U.S. Pat. No. (method of inserting DNA into living cells): McCormick et al., U.S. Pat. No. 5,677,178 (use of cytopathic viruses); and U.S. Pat. No. 5,928,913 (vectors for gene delivery), as well as other documents cited herein.

A viral vector, for instance, selected from pig herpes viruses, such as Aujeszky's disease virus, porcine adenovirus, poxviruses, especially vaccinia virus, avipox virus, canarypox virus, and swinepox virus, as well as DNA vectors (DNA plasmids) are advantageously employed in the practice of the invention.

Methods of Producing the H5 Proteins According to the Present Invention

According to another aspect, the present invention provides methods of producing and/or recovering high amounts of recombinant H5 protein: i) by permitting infection of susceptible cells in culture with a recombinant viral vector containing H5 DNA coding sequences, wherein H5 protein is expressed by the recombinant viral vector, and ii) thereafter recovering the H5 protein from cell culture. High amounts of H5 protein means, but are not limited to, more than about 20 µg/mL cell culture, preferably more than about 25 μg/mL, even more preferred more than about 30 μg/mL, even more preferred more than about 40 μg/mL, even more preferred more than about 50 μg/mL, even more preferred more than about 60 μg/mL, even more preferred more than about 80 μg/mL, even more preferred more than about 100 μg/mL, even more preferred than about 150 μg/mL, most preferred more than about 190 μg/mL.

According to a preferred embodiment, the H5 protein is recovered by harvesting the whole (i.e. intact) SF+ cells expressing the H5 protein.

Preferred cells are those susceptible for infection with an appropriate recombinant viral vector, containing a H5 DNA and expressing the H5 protein. Preferably the cells are insect cells, and more preferably, they include the insect cells sold under the trademark SF+ insect cells (Protein Sciences Corporation, Meriden, Conn.). Preferred cell cultures have a cell count between about 0.3-2.0×$10^6$ cells/mL, more preferably from about 0.35-1.9×$10^6$ cells/mL, still more preferably from about 0.4-1.8×$10^6$ cells/mL, even more preferably from about 0.45-1.7×$10^6$ cells/mL, and most preferably from about 0.5-1.5×$10^6$ cells/mL.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems will work for purposes of the present invention, namely the expression of HG into the supernatant of a cell culture. Such other expression systems may require the use of a signal sequence in order to cause H5 expression into the media.

Appropriate growth media will also be determinable by those of skill in the art with a preferred growth media being serum-free insect cell media such as Excell 420 (JRH Biosciences, Inc., Lenexa, Kans.) and the like.

The recombinant viral vector containing the HG DNA sequences has a preferred multiplicity of infection (MOI) of between about 0.03-1.6° more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of 0.35-1.9×$10^6$ cells/mL, still more preferably of about 0.4-1.8×$10^6$ cells/mL, even more preferably of about 0.45-1.7×$10^6$ cells/mL, and most preferably of about 0.5-1.5×$10^6$ cells/mL with a recombinant viral vector containing a H5 DNA and expressing the H5 protein having a MOI (multiplicity of infection) of between about 0.03-1.5, more preferably from about 0.05-1.3, still more preferably from about 0.09-1.1, and most preferably from about 0.1-1.0.

The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C. even more preferably from about 26-28° C., and most preferably about 27° C. Preferably, the SF+ cells are observed following inoculation for characteristic baculovirus-induced changes. Such observation may include monitoring cell density trends and the decrease in viability during the post-infection period. It was found that peak viral titer is observed 3-5 days after infection and peak H5 protein expression in the cells is obtained between days 5 and 8, and/or when cell viability decreases to less than 10%.

Thus, one aspect of the present invention provides a method of producing and/or recovering recombinant H5 protein, preferably in amounts described above, by i) permitting infection of a number of susceptible cells (see above) in culture with a recombinant viral vector with a MOI as defined above, ii) expressing H5 protein by the recombinant viral vector, and iii) thereafter recovering the H5 protein from the cells obtained between days 5 and 8 after infection and/or cell viability decreases to less then 10%. Preferably, the recombinant viral vector is a recombinant baculovirus containing H5 DNA coding sequences and the cells are SF+ cells. Additionally, it is preferred that the culture be periodically examined for macroscopic and microscopic evidence of contamination or for atypical changes in cell morphology during the post-infection period. Any culture exhibiting any contamination should be discarded.

For recovery of H5 protein that will be used in an immunogenic or immunological composition such as a vaccine, the inclusion of an inactivation step is preferred in order to inactivate the viral vector.

An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Thus, the present invention also relates to a method of producing and/or recovering recombinant H5 protein, preferably in amounts described above, by i) permitting infection of a number of susceptible cells (see above) in culture with a recombinant viral vector with a MOI as defined above, ii) expressing H5 protein by the recombinant viral vector, iii) recovering the H5 expressed in cells obtained between days 5 and 8 after infection and/or cell viability decreases to less then 10%, and iv) inactivating the recombinant viral vector.

Preferably, this inactivation is done either just before or just after the filtration step, with after the filtration step being the preferred time for inactivation. Any conventional inactivation method can be used for purposes of the present invention. Thus, inactivation can be performed by chemical and/or physical treatments. In preferred forms, the volume of harvest fluids is determined and the temperature is brought to between about 32-42° C., more preferably between about 34-40° C., and most preferably between about 35-39° C. Preferred inactivation methods include the addition of cyclized binary ethylenimine (BEI), preferably in a concentration of about 1 to about 20 mM, preferably of about 2 to about 10 mM, still more preferably of about 2 to about 8 mM, still more preferably of about 3 to about 7 mM, most preferably of about 5 mM. For example the inactivation includes the addition of a solution of 2-bromoethyleneamine hydrobromide, preferably of about 0.4M, which has been cyclized to 0.2M binary ethylenimine (BEI) in 0.3N NaOH, to the fluids to give a final concentration of about 5 mM BEI. Preferably, the fluids are then stirred continuously for 72-96 hours and the inactivated harvest fluids can be stored frozen at −40° C. or below or between about 1-7° C. After inactivation is completed a sodium thiosulfate solution, preferably at 1.0M is added to neutralize any residual BEI. Preferably, the sodium thiosulfate is added in equivalent amount as compared to the BEI added prior to for inactivation. For example, in the event BEI is added to a final concentration of 5 mM, a 1.0M sodium thiosulfate solution is added to give a final minimum concentration of 5 mM to neutralize any residual BEI.

Thus, one further aspect of the present invention relates to a method of producing recombinant H5 protein, preferably in amounts described above, by i) permitting infection of a number of susceptible cells (see above) in culture with a recombinant viral vector with a MOI as defined above, ii) expressing H5 protein by the recombinant viral vector, iii) recovering the H5 expressed in the cells obtained between days 5 and 8 after infection and/or cell viability decreases to less then 10%, and iv) inactivating the recombinant viral vector. Preferably, the recombinant viral vector is a baculovirus containing H5 DNA coding sequences and the cells are SF+ cells. Preferred inactivation steps are those described above. Preferably, inactivation is performed between about 35-39° C. and in the presence of 2 to 8 mM BEI, still more preferred in the presence of about 5 mM BEI.

According to one further aspect of the present invention, the method described above also includes a neutralization step after step iv). This step v) comprises adding of an equivalent amount of an agent that neutralizes the inactivation agent within the solution. Preferably, if the inactivation agent is BEI, addition of sodium thiosulfate to an equivalent amount is preferred. Thus, according to a further aspect, step v) comprises adding of a sodium thiosulfate solution to a final concentration of about 1 to about 20 mM, preferably of about 2 to about 10 mM, still more preferably of about 2 to about 8 mM, still more preferably of about 3 to about 7 mM most preferably of about 5 mM, when the inactivation agent is BEI.

In preferred forms and especially in forms that will use the recombinant H5 protein in an immunogenic composition such as a vaccine, each lot of harvested H5 protein will be tested for inactivation by passage in the anchorage dependent, baculovirus susceptible insect cells, such as Sf9 cells. In a preferred form of this testing, 150 cm of appropriate cell culture monolayer is inoculated with 1.0 mL of inactivated H5 fluids and maintained at 25-29° C. for 14 days with at least two passages. At the end of the maintenance period, the cell monolayers are examined for cytopathogenic effect (CPE) typical of H5 baculovirus. Preferably, positive virus controls are also used. Such controls can consist of one culture of Sf9 cells inoculated with a non-inactivated reference H5 baculovirus and one flask of Sf9 cells that remain non-inoculated. After incubation and passage, the absence of virus-infected cells in the BEI treated viral fluids would constitute a satisfactory inactivation test. The control cells inoculated with the reference virus should exhibit CPE typical of H5 baculovirus and the non-inoculated flask should not exhibit any evidence of H5 baculovirus CPE. Alternatively, at the end of the maintenance period, the supernatant samples could be collected and inoculated onto a Sf9 96 well plate, which has been loaded with Sf9 cells, and then maintained at 25-29° C. for 5-6 days. The plate is then fixed and stained with anti-H5 antibody conjugated to FITC or any labeled antibody directed to baculovirus specific proteins (i.e. gp64). The absence of CPE, H5 expression, 010 or expression of baculovirus specific proteins (i.e. gp64) in the BEI treated viral fluids constitutes a satisfactory inactivation test. The control cells inoculated with the reference virus should exhibit CPE and IFA activity and the non-inoculated flask should not exhibit any evidence of H5 baculovirus CPE and contain no ISA activity.

Thus a further aspect described herein, relates to an inactivation test for determining the effectiveness of the inactivation of the recombination viral vector expressing H5 protein, comprises the steps: i) contacting at least a portion of the culture fluid containing the recombinant viral vector with an inactivating agent, preferably as described above, ii) adding a neutralization agent to neutralize the inactivation agent, preferably as described above, and iii) determining the residual infectivity by the assays as described above.

After inactivation, the relative amount of recombinant H5 protein in a sample can be determined in a number of ways. Preferred methods of quantitation include SDS-PAGE densitometry, ELISA, and animal vaccination studies that correlate known quantities of vaccine with clinical outcomes (serology, etc.). When SOS-PAGE is utilized for quantitation, the sample material containing an unknown amount of recombinant H5 protein is run on a gel, together with samples that contain different known amounts of recombinant H5 protein. A standard curve can then be produced based on the known samples and the amount of recombinant H5 in the unknown sample can be determined by comparison with this standard curve. Because ELISAs are generally recognized as the industry standard for antigen quantitation, they are preferred for quantitation.

Vaccines Comprising H5 Proteins or Nucleic Acid Molecules or Vectors Coding for Those According to a further aspect, the present invention relates to vaccines or pharmaceutical compositions in general, that comprises,
  i. one or more of the H5 proteins as described herein,
  ii. one or more of the nucleic acid molecules as described herein, coding for any such H5 proteins; and/or
  iii. one or more of the vectors as described herein, including any such nucleic acid molecules and coding for any such H5 proteins as described herein; and
  iv. a pharmaceutical acceptable carrier and/or excipient.

The term "pharmaceutical composition" "Pharmaceutical/vaccine composition" as described herein, includes but is not limited to, vaccines for the reduction or prevention of an infection or to a composition of matter for the treatment and lessening of an infection.

The preparation of nucleic acid based vaccines, preferably cDNA vaccines, coding for influenza hemagglutinin are described for example in Deck et al., *Vaccine* 1997; 15(1):71-78; Ulmer et al., *Science* 1993; 259:1745-1749, Ulmer et al., *Vaccine* 1994-12(16):1541-1544. Any of those methods can be used for the production of nucleic acid based vaccines, preferably cDNA vaccines, coding for an influenza H5 protein as described herein.

Moreover, a vaccine, which comprises H5 protein or parts thereof as described herein, can be produced by conventional approaches, e.g. by recombinant expression techniques or by biochemical purification and separation techniques. Recombinant expression techniques, including the expression in insect cells are well known in the art, and described for example in Sambrook et al., *Molecular Cloning: A Laboratory Manual, Second Edition* (1989) Cold Spring Harbor Laboratory Press, Cold Spring Harbor, N.Y.; *DNA Cloning; A Practical Approach, Volumes I and II* (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]: *Animal Cell Culture* [R. I. Freshney, ed. (1986)]; *Immobilized Cells And Enzymes* [IRL Press, (1986)]; B, Perbal, *A Practical Guide To Molecular Cloning* (1984); F. M. Ausubel et al. (eds.), *Current Protocols in Molecular Biology*, John Wiley & Sons, Inc. 1994). Further examples of well established recombinant expression systems are bacterial expression systems such as *E. coli* or *B. subtilis*, yeast-based expression systems such as *S. cerevisiae* or *S. pombe*, or mammalian cell expression systems such as the BHK-, CHO- and/or NSO-based expression systems. Such systems are well known in the art and generally available, e.g. commercially through Clontech Laboratories, Inc. 4030 Fabian Way, Palo Alto, Calif. 94303-4607, USA. Further expression strategies are for example described in Lüschow et al., *Vaccine* no. 19 (2001), pp. 4249-4259, or Veit et al., *PNAS* vol. 103 (2006), pp. 8197-8202. Furthermore, recombinant adeno-associated virus systems are well established and for example described in U.S. Pat. No. 5,436,146 or WO200203872 with further references. Moreover, vaccinia (pox) virus based expression systems, for example as described in U.S. Pat. No. 6,265,183 with further references, are also well established and suitable to produce recombinant antigen(s), antigenic composition(s) as used according to the invention. Further suitable expression systems make use of recombinant popova viruses, such as SV40, fowl pox virus, pseudorabies viruses and retroviruses.

The relevant pharmaceutical/vaccine compositions as described herein, can also comprise inactivated virus which comprises H5 protein as described herein, an apathogenic version of a live virus comprising H5 protein as described herein, preparation and/or fragments of a virus, wherein said preparation and/or fragment comprise the H5 protein as described herein.

The skilled person knows additional components which may be comprised in said compositions/vaccines together with antigen (see for example, *Remington's Pharmaceutical Sciences*. (1990). 18th ed. Mack Publ., Easton). The expert may use known injectable, physiologically acceptable sterile solutions. For preparing a ready-to-use solution, aqueous isotonic solutions, such as e.g. saline or corresponding plasma protein solutions are readily available. The pharmaceutical composition/vaccine may be present as lyophylisates or dry preparations, which can be reconstituted with a known injectable solution directly before use under sterile conditions, e.g. as a kit of palls.

In addition the pharmaceutical/vaccine compositions of the present invention can include one or more veterinary-acceptable carriers. As used herein, "a veterinary-acceptable carrier" includes but is not limited to any and all solvents, dispersion media, coatings, adjuvants, stabilizing agents, diluents, preservatives, antibacterial and antifungal agents, isotonic agents, adsorption delaying agents, and the like.

Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

A preservative as used herein, refers to an anti-microbiological active agent, such as for example Gentamycin, Merthiolate, and the like. In particular adding of a preservative is most preferred for the preparation of a multi-dose composition. Those anti-microbiological active agents are added in concentrations effective to prevent the composition of interest for any microbiological contamination or for inhibition of any microbiological growth within the composition of interest.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion.

The emulsion can be based in particular on light liquid paraffin oil (European Pharmacopoeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed Stewart-Tull, D. E. S.). John Wiley and Sons, NY, pp 54-94 (1995) and Todd et al., Vaccine 15:564-570 (1997). Examples for suitable oil-in water emulsions are EMULSIGEN®-based adjuvants, such as EMULSIGEN® (a oil-in-water emulsion (o/w)), EMULSIGEN-D® (a oil-in-water (o/w) with dimethyldioctadecylammonum bromide (DDA)), EMULSIGEN-P® (a oil-in-water (o/w) with a proprietary immunostimulant), EMULSIGEN-75® (a double adjuvants comprise of a oil-in-water (o/w) with a crosslinked polymer) (MVP Laboratories, Inc. Omaha, Nebr., USA). It has been surprisingly found, that pharmaceutical/vaccine compositions that comprise H5 protein, preferably recombinant H5 protein as described herein, have been effectively adjuvanted with oil-in water emulsions, preferably with such EMULSIGEN®-based adjuvants, more preferably with EMULSIGEN-P® (a oil-in-water (o/w) with a proprietary immunostimulant) and EMULSIGEN-D® (a oil-in-water (o/w) with dimethyldioctadecylammonum bromide (DDA)).

Moreover, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2: June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (also known as polyacrylic acid); (BF Goodrich, Ohio, USA) are particularly appropriate. They are cross-linked with an allyl sucrose or with allyl pentaerythritol. Among then, there may be mentioned Carbopol®974P (also known as polyacrylic acid), Carbopol®934P (also known as polyacrylic acid) and Carbopol®971P (also known as polyacrylic acid). Most preferred is the use of Carbopol®971P (also known as polyacrylic acid). Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, or muramyl dipeptide among many others.

Preferably, the adjuvant is added in an amount of about 100 μg to about 10 mg per dose. Even more preferred the adjuvant is added in an amount of about 100 μg to about 10 mg per dose. Even more preferred the adjuvant is added in an amount of about 500 μg to about 5 mg per dose. Even more preferred the adjuvant is added in an amount of about 750 μg to about 2.5 mg per dose. Most preferred the adjuvant is added in an amount of about 1 mg per dose.

The pharmaceutical/vaccine compositions, can further include one or more other immunomodulatory agents such as, e.g., interleukins, interferons, or other cytokines. The pharmaceutical/vaccine compositions can also include Gentamicin and Merthiolate. While the amounts and concentrations of adjuvants and additives useful in the context of the present invention can readily be determined by the skilled artisans the present invention contemplates compositions comprising from about 50 μg to about 2000 μg of adjuvant and preferably about 250 ug/1 ml dose of the vaccine composition. In another preferred embodiment, the present invention contemplates vaccine compositions comprising from about 1 ug/ml to about 60 μg/ml of antibiotics, and more preferably less than about 30 μg/ml of antibiotics.

Thus according to a further embodiment, the present invention also relates to a pharmaceutical/vaccine composition comprising i. a therapeutically effective amount of any one of the H5 proteins of influenza virus as described herein wherein the H5 protein having the amino acid 223N and the modification 328K+, wherein numbering of the amino acid positions of the H5 protein refers to the amino acid position as exemplarily given in SEQ ID NO:1 and wherein the modification 328K+ means that at amino acid position 328 of H5 protein a second Lysine (K+) is inserted and ii. a pharmaceutically acceptable adjuvants as described above.

Preferably, the adjuvant is selected from the group consisting of:

a) EMULSIGEN®, a oil-in-water emulsion (o/w);
b) EMULSIGEN-D®, a oil-in-water (o/w) with dimethyldioctadecylammonum bromide (DDA);
c) a Polygen, a copolymer
d) EMULSIGEN-P®, a oil-in-water (o/w) with a proprietary immunostimulant e) Carbigen is a cross-linked polymer
f) EMULSIGEN-78' a double adjuvants comprise of a oil-in-water (o/w) with a cross-linked polymer
g) ISA 70 is a water-in-oil (w/o)

Most preferably, the adjuvants is a oil-in-water emulsion such as an emulsigen-based adjuvant selected from the group consisting of EMULSIGEN®, EMULSIGEN-D®, EMULSIGEN-P®, EMULSIGEN-75®, EMULSIGEN® and EMULSIGEN-P®. Most preferably EMULSIGEN® and EMULSIGEN-P® are used in the formulation of the current invention.

According to a further aspect, the pharmaceutical/vaccine compositions as provided herewith, comprise one or more antigen. Preferably, that further antigen is an antigen of a poultry or mammalian pathogen. According to a further embodiments, that additional antigen is an further influenza antigen such as hemagglutinin H3, H7, H9, or any other hemagglutinin of influenza virus. The additional antigen(s) can be added in a purified form, as part of an antigenic preparation, in form of a killed microorganism or in form of a modified live microorganism.

The term "antigen", as used herein means, but is not limited to, peptides, polypeptides, glycopeptides, or polysaccharides which are capable of specifically interacting with an antigen recognition molecule of the immune system, such as an immunoglobulin (antibody) or T cell antigen receptor in order to elicit, activate or stimulate an immune response directed to said antigen in a host to which said antigen is administered. The term "antigen" also refers to nucleic acid molecules, preferably DNA- or RNA-molecules, each of which codes for and express a peptide, polypeptide, or glycopeptide that is capable of specifically interacting with an antigen recognition molecule of the immune system, such as an immunoglobulin (antibody) or T cell antigen receptor in order to elicit, activate or stimulate an immune response against the antigen that is coded by the nucleic acid molecule. The antigen used for the preparation of the pharmaceutical composition which is used according to the invention is a microorganism or an antigenic part and/or preparation of said microorganism. In this connection, the term "immunization", as used herein, means but is not limited to, any cause or enhancement of an immune response. The term "immune response" is already described supra.

Administration strategies for influenza vaccines are well known in the art. Mucosal vaccination strategies for inactivated and attenuated virus vaccines are contemplated. While the mucosa can be targeted by local delivery of a vaccine, various strategies have been employed to deliver immunogenic proteins to the mucosa.

In a specific embodiment, the vaccine can be administered in an admixture with, or as a conjugate or chimeric fusion protein with, cholera toxin, such as cholera toxin B or a cholera toxin A/B chimera (Hajishengallis, *J Immunol.*, 154:4322-32, 1995; Jobling and Holmes, *Infect Immun.*, 60:4915-24, 1992). Mucosal vaccines based on use of the cholera toxin B subunit have been described (Lebens and Holmgren, *Dev Biol Stand* 82,215-27, 1994). In another embodiment, an admixture with heat labile enterotoxin (LT) can be prepared for mucosal vaccination.

Other mucosal immunization strategies include encapsulating the virus in microcapsules (U.S. Pat. No. 5,075,109, U.S. Pat. No. 5,820,883, and U.S. Pat. No. 5,853,763) and using an immunopotentiating membranous carrier (WO 98/0558). Immunogenicity of orally administered immunogens can be enhanced by using red blood cells (rbc) or rbc ghosts (U.S. Pat. No. 5,643,577), or by using blue tongue antigen (U.S. Pat. No. 5,690,938).

According to another aspect, the present invention relates to a method for preparing a pharmaceutical/vaccine composition as described above, preferably a method for producing a vaccine which comprises a recombinant, baculovirus expressed H5 protein as described supra. Generally, this method includes the steps of transfecting a construct into a virus, wherein the construct comprises I) recombinant H5 cDNA as described herein, ii) infecting cells in growth media with the transfected virus, iii) causing the virus to express the recombinant H5 protein as described herein iv) recovering the expressed H5 protein from the culture v) and preparing the composition by blending the expressed H5 protein with a suitable adjuvant and/or other pharmaceutically acceptable carrier.

Preferred adjuvants are those described above. Thus according to a further aspect, the method for preparing an antigenic composition, such as for example a vaccine, for invoking an immune response against influenza infections comprises i) preparing and recovering H5 protein, and it) admixing this with a suitable adjuvants.

In addition, the vaccine composition of the present invention can also include diluents, isotonic agents, stabilizers, an/or preservatives. Diluents can include water, saline, dextrose, ethanol, glycerol, and the like. Isotonic agents can include anorganic or organic salts, e.g. sodium chlonde, dextrose, mannitol, sorbitol, and lactose, saccharides, trehalose, mannitol, saccharose among others. Stabilizers include albumin and alkali salts of ethylendiamintetracetic acid, among others. Suitable adjuvants, are those described above.

Medicinal Use of any of Such H5 Proteins, Nucleic Acid Molecules, Vectors and Vaccines The H5 proteins as provided herewith, the nucleic acid molecules coding for any such H5 proteins, the vectors comprising any such nucleic acid molecules coding for any such H5 proteins as described herein, and any pharmaceutical/vaccine composition comprising any of such H5 protein, nucleic acid molecule or vector can be used as a medicine, preferably for the treatment and prophylaxis of infections, caused by influenza virus, most preferably by influenza A virus. The H5 proteins as provided herewith, the nucleic acid molecules encoding for any such H5 proteins, the vectors comprising any such nucleic acid molecules encoding for any such H5 proteins as described herein, and any pharmaceutical/vaccine composition comprising any of such H5 protein, nucleic acid molecule or vector, as described herein, can be used for the treatment or prophylaxis of human beings as well as in veterinary medicine. When used in veterinary medicine, the treatment of poultry, preferably bird, chicken, duck, turkey and the like as well as mammals, preferably pigs, cattle, horses, seals, camels, dogs, cats, hamsters, mice and the like, is preferred.

Thus, according to another aspect the present invention relates to the use of H5 proteins as provided herewith, the nucleic acid molecules encoding for any such H5 proteins, the vectors comprising any such nucleic acid molecules encoding for any such H5 proteins as described herein and any pharmaceutical/vaccine compositions comprising any of such H5 protein, nucleic acid molecule or vector as described herein, can be used as a medicine, preferably as a medicine for human beings and/or as veterinary medicine.

Moreover, H5 proteins as provided herewith, the nucleic acid molecules coding for any such H5 proteins, the vectors comprising any such nucleic acid molecules coding for any such H5 protein, as described herein, can be used for the preparation of a pharmaceutical composition, as described herein, for the prophylaxis or treatment of infections caused by viral influenza. As mentioned above, those pharmaceutical compositions/vaccine compositions can be used for the treatment and/or prophylaxis of human beings as well as for the treatment and/or prophylaxis of animals, such as poultry, preferably bird, chicken, duck, turkey and the like as well as mammals, preferably pigs, cattle, horses, seals, camels, dogs, cats, hamsters, mice and the like.

H5 proteins as provided herewith, the nucleic acid molecules coding for any such H5 proteins, the vectors comprising any such nucleic acid molecules coding for any such H5 proteins, as described herein, can be used for the preparation of a pharmaceutical composition, as described herein, are suitable for the treatment and prophylaxis of viral influenza infection, which preferably are caused by avian, swine or human influenza virus or any combination or hybrid thereof.

According to a further aspect, the present invention also relates to a method for the treatment or prophylaxis of influenza virus infections, wherein the method comprising administration of a therapeutically effective amount of the H5 protein as describe herein, to a subject in need of such a treatment. Moreover, the present invention also relates to a method for the treatment or prophylaxis of influenza virus infections, wherein the method comprising administration of a therapeutically effective amount of any H5 nucleic acid molecule or vector as described herein, that codes for any H5 protein as described herein, to a subject in need of such a treatment. Furthermore, the present invention also relates to a method for the treatment or prophylaxis of influenza virus infections, wherein the method comprising administration of a therapeutically effective amount of the vaccine comprising any such H5 protein, nucleic acid molecule or vector, as described herein, to a subject in need of such a treatment. The subject in need thereof can be a human being as well as an animal, preferably poultry, even more preferably bird, chicken, duck, turkey or a mammal, preferably pig, cattle, horse, seal, camel, dog, cat, hamster, mouse and the like.

Preferably, when chicken are vaccinated, the H5 protein as described herein can be used for vaccination at day 1 of age or later, e.g. at day 10, or at day 1 to 10, or at day 10 or later.

Preferably the influenza infection that can be treated by the administration of any H5 protein, the nucleic acid molecule or vector encoding for any such H5 protein, or any pharmaceutical/vaccine compositions as described herein, is caused by avian, swine or human influenza virus or any combination or hybrid thereof.

According to another aspect, the present invention relates to a kit of parts, that comprises i) any of such H5 protein as described herein, the nucleic acid molecule or vector encoding for any such H5 protein, or any pharmaceutical/vaccine composition comprising any of such H5 protein, nucleic acid molecule or vector as described herein, 010 and ii) a package leaflet indicating the use of such H5 protein, nucleic acid molecule, vector or vaccine for the treatment or prophylaxis of infections caused by influenza virus. When chicken are vaccinated, the H5 protein as described herein can be used for vaccination at day 1 on age or later.

According to a further embodiment, that kit in parts comprises at least one further antigen of a poultry or mammalian pathogen and the information indication the medicinal, human or veterinary use of that additional antigen.

EXAMPLES

The following examples set forth preferred materials and procedures in accordance with the present invention. It is to be understood, however, that these examples are provided by way of illustration only, and nothing therein should be deemed a limitation upon the overall scope of the invention.

Example 1

Construction of a Recombinant Baculoviruses Coding for and Expressing HA H5 Antigens The recombinant baculovirus containing the H5 HA antigen was generated as follows: the coding sequences of the H5 HA (SEQ ID NO:2) was chemically synthesized and subcloned into the transfer vector pVL1392 (BD Biosciences Pharmingen, San Diego, Calif.). The H5 HA MutK+ (SEQ ID NO:4) was generated by using oligonucleotide primers and the QUIKCHANGE® Site-Directed Mutagenesis Kit (Stratagene, La Jolla, Calif.) and subcloned into the transfer vector pVL1392 (BD Biosciences Pharmingen, San Diego, Calif.). The pVL1392 plasmids containing the genes coding for H5 HA antigen (SEQ ID NO:2) and H5 HA MutK+ (SEQ ID NO:4) were then co-transfected with DIAMONDBAC® (Sigma) baculovirus DNA into Sf9 insect cells (BD Biosciences Pharmingen) to generate the recombinant baculovirus containing the genes H5 HA coding for SEQ ID NO:2 and H5 HA mutK+ coding for SEQ ID NO:4. The recombinant baculoviruses containing the genes coding for H5 HA (SEQ ID NO:2) and H5 HA MutK+ (SEQ ID NO:4) were plaque-purified and Master Seed Viruses (MSVs) were propagated on the SF+ cell line, aliquoted, and stored at −70° C. Insect cells infected with H5 HA baculoviruses as described above to generate MSV or Working Seed Viruses express H5 HA antigen (SEQ ID NO:2) and H5 HA MutK+ (SEQ ID NO:4) antigen as detected by polyclonal serum or monoclonal antibodies in an indirect fluorescent antibody assay or Western blot.

After being seeded with the appropriate amounts of recombinant baculoviruses (H5 HA and H5 HA MutK+, respectively), spinner flasks containing SF+ cells (Protein Sciences, Inc., Meriden, Conn.) were then incubated at 27±2° C. for 7 days and with stirring 100 rpm during that time. The flasks used ventilated caps to allow for air flow. The crude whole cell culture containing baculovirus infected SF+ cells and the cell culture supernatents of each culture were harvested.

Example 2

Preparation of Pharmaceutical Compositions (Vaccines) Comprising HA H5 Antigens

The crude whole cell H5 HA protein and H5 HA Mutk+ protein expressed in insect cells by baculovirus-based expression system were harvested. Baculoviruses were inactivated in the presence of 5 mM cyclized binary ethylenimine (BEI) (final concentration) between about 32 and 3° C. for 72 to 96 hours. After inactivation is completed a 0.3 M sodium thiosulfate solution was added to a final concentration of 5 mM to neutralize any residual BEI. After neutralization various adjuvants were added and the following vaccine/pharmaceutical compositions were generated.

| VACCINES | |
|---|---|
| Generic product name | 501 |
| Antigen | Crude whole-cell H5 HA protein expressed in insect cells by a baculovirus-based expression system. |

-continued

VACCINES

| | |
|---|---|
| Formulation | An experimental vaccine comprised of cultured insect cells and supernatant expressing recombinant H5 HA. The vaccine was adjuvanted with EMULSIGEN ®. |
| Generic product name | 502 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with EMULSIGEN-D ®. |
| Generic product name | 503 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with POLYGEN ™. |
| Generic product name | 504 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with EMULSIGEN-P ®. |
| Generic product name | 505 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with CARBIGEN ™. |
| Generic product name | 506 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with EMULSIGEN-75 ®. |
| Generic product name | 507 |
| Antigen | Crude whole-cell H5 HA protein expressed in insect cells by a baculovirus-based expression system. |
| Formulation | An experimental vaccine comprised of cultured insect cells and supernatant expressing recombinant H5 HA. The vaccine was adjuvanted with ISA 70. |
| Generic product name | 508 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with EMULSIGEN. |
| Generic product name | 509 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with EMULSIGEN-D ®. |
| Generic product name | 510 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with POLYGEN ™. |
| Generic product name | 511 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with EMULSIGEN-P ®. |
| Generic product name | 512 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted with CARBIGEN ™. |
| Generic product name | 513 |
| Antigen | Crude whole-cell H5 HA mutK+ protein expressed in insect cells by a baculovirus-based expression system. |
| Formulation | An experimental vaccine comprised of cultured insect cells and supernatant expressing recombinant H5 HA. The vaccine was adjuvanted withEMULSIGEN-75 ®. |

Example 3

Vaccination of Swine (Pigs) Against Avian Influenza

1. Introduction

The purpose of this study was to determine the ability of experimental vaccines containing a crude extract of recombinant H5 hemagglutinin (HA) antigen to induce hemagglutination inhibition (HI) titers in swine. Various adjuvants were evaluated with the H5 HA antigens.

The HA H5 prototypes evaluated in this study contained antigen from either conventional H5 HA or H5 HA MutK+, Conventional H5 HA was derived from A/duck/China/E319-2/03, whereas H5 HA MutK+ consists of conventional H5 HA which was engineered to contain three specific amino acid changes at S120N, D150N, S223N and 328mutK+. It also contains amino acid 94N. The particular amino acid changes in H5 HA Mut K+ result in a H5 HA that more closely resembles the HA of A/HK/213/03. The amino acid composition of the H5 HA of A/HK/213/03 is currently thought to aid in antibody recognition of the H5 HA.

2. Study Design:

TABLE 1

Study Overview.

| Group | Number of Pigs | Vaccine Prototype | Day 0 | Day 21 | Day 35 |
|---|---|---|---|---|---|
| 1 | 5 | 501 | Bleed and Vaccinate Intramuscularly (brachiocephalic group) by administration of 1 ml in the LEFT side of the neck.) | Bleed and Vaccinate Intramuscularly (brachiocephalic group) by administration of 1 ml in the RIGHT side of the neck.) | Bleed and Terminate Study |
| 2 | 5 | 502 | | | |
| 3 | 5 | 503 | | | |
| 4 | 5 | 504 | | | |
| 5 | 5 | 505 | | | |
| 6 | 5 | 506 | | | |
| 7 | 5 | 507 | | | |
| 8 | 5 | 508 | | | |
| 9 | 5 | 509 | | | |
| 10 | 5 | 510 | | | |

TABLE 1-continued

Study Overview.

| Group | Number of Pigs | Vaccine Prototype | Day 0 | Day 21 | Day 35 |
|---|---|---|---|---|---|
| 11 | 5 | 511 | | | |
| 12 | 5 | 512 | | | |
| 13 | 5 | 513 | | | |
| 14 | 5 | 514 | | | |
| 15 | 5 | None | Bleed | Bleed | |

The piglets were 3 weeks±5 days of age at the beginning of the study. The piglets were clinically healthy at the beginning of the study. Blood samples were obtained on Study Days 0, 21, and 35.

All study animals were observed daily on Study Days 1 through 35 in regard to the general health status. For seven days following each vaccination, injection sites were investigated daily and visible reactions were recorded. At the conclusion of the animal phase of the study on Study Day 35, all animals were humanely euthanized.

3. Vaccines

Vaccines 501 to 514 as described in EXAMPLE 2 were used for the pig vaccination study.

4. Hemagglutinin Inhibition Assay

Swine were vaccinated with the H5 HA-containing prototypes on Days 0 and 21 Swine sera were collected for evaluation by hemagglutination inhibition (HI) assay on Days 0, 21, 35. The HI assay was performed to detect the presence of HA-specific antibodies. A heterologous H5N2 virus, A/chicken/Mexico/232/94, was used at a concentration of four hemagglutinating units [4 HA units] in the HI assay. In U-bottomed microtiter plates serial two-fold serum dilutions in PBS were subsequently mixed with equal volumes (25 µL) containing 4 HA units of virus, and incubated at room temperature (about 25° C.) for 30 min., Chicken red blood cells, at a concentration of 0.5% in PBS, were added to the serum-virus containing wells and incubated for 40 min at room temperature. The HI titers were determined as reciprocals of the highest serum dilutions in which inhibition of hemagglutination was observed, 5. Results HI test used the Mexican government official H5N1 antigen (A/chicken/Mexico/232/94) [4 HA Units] Vaccination regimen of 1×1 mL on Days 0 and 21.

| | | HI Titers | | |
|---|---|---|---|---|
| | | Day 0 | Day 21 | Day 35 |
| 501 | H5 - EMULSIGEN ® | 0 | 0 | 4 |
| 502 | H5 - EMULSIGEN-D ® | 0 | 0 | 4 |
| 503 | H5 - POLYGEN ™ | 0 | 0 | 0 |
| 504 | H5 - EMULSIGEN-P ® | 0 | 0 | 2 |
| 505 | H5 - CARBIGEN ™ | 0 | 0 | 4 |
| 506 | H5 - EMULSIGEN-75 ® | 0 | 0 | 16 |
| 507 | H5 ISA 70 | 0 | 0 | 16 |
| 508 | H5 K+ - EMULSIGEN ® | 0 | 0 | 128 |
| 509 | H5 K+ - EMULSIGEN-D ® | 0 | 0 | 64 |
| 510 | H5 K+ - POLYGEN ™ | 0 | 0 | 16 |
| 511 | H5 K+ - EMULSIGEN-P ® | 0 | 0 | 0 |
| 512 | H5 K+ - CARBIGEN ™ | 0 | 0 | 0 |
| 513 | H5 K+ - EMULSIGEN-75 ® | 0 | 0 | 16 |
| 514 | H5 K+ - ISA 70 | 0 | 4 | 32 |
| Control | None | 0 | 0 | 0 |

BIV H5 (derived from Influenza A virus (A/duck/China/E319-2/03(H5N1))
BIV H5 K+ (mutated BIV H5 to include S120N, D155N, S223N, and added 328K+)

The results demonstrate that most of the vaccine compositions elicit an immune response in the vaccinated pigs. In particular, most of the vaccine compositions result in a seroconversion, which means most of the vaccinated pigs developed specific antibodies against the avian influenza virus used in the HI assay. Altogether, the results clearly and undoubtedly prove that the claimed inventive idea works very well. The risk of pandemic infection of pigs (animal of a second species), with avian influenza virus (pathogen of a first species) can dramatically be reduced by the vaccination of pigs with a relevant antigen of avian influenza virus. This has been clearly demonstrated. Moreover, by this vaccination concept, the transmission and adaptation of avian influenza virus to mammals, including human beings is dramatically reduced. Pigs are one of the most important reservoirs for avian pathogens, including avian influenza virus. If the virus replication in pigs and therefore the risk of adaptation of avian influenza to pigs is dramatically reduced and controlled, the risk for any adaptation of avian influenza virus to human beings is also dramatically reduced. In case, where the administration of antigen results in lower HI titer, which means titer lower than 30, further boosts with antigen will be required to further improve the HI titer and to enhance the immune protection in the vaccinated pigs. Therefore, low titer does not mean that no protection can be achieved, it only teach that further boosts seems to be required to improve the immune response. The fact, that an immune response could be measured in vaccinated pigs demonstrates that the inventive idea underlying the present invention works very well. In other words, the experiments provided herewith clearly and undoubtedly give evidence that the inventive idea of the present invention works.

Example 4

Vaccination of Birds Against Avian Influenza

1. Introduction

The purpose of this study was to determine the ability of experimental vaccines containing a crude extract of recombinant H5mutk+ hemagglutinin (H5 HA mutk+) antigen to induce hemagglutination inhibition (HI) titers in chicken. In addition, a conventional recombinant H5 antigen (H5 HA) as well as the inactivated vaccine VOLVAC®AI (Boehringer Ingelheim Vetmedica, Mexico) were used for control. Moreover, various adjuvants were evaluated with the H5 HA antigens.

2. Study Design:

SPF birds (15-25) were vaccinated independently with different experimental vaccines at 1 or 10 days of age by subcutaneous route with 0.6 ml in the back of the neck; all the birds were maintained in isolators during the experiment. Feed and water were provided ad libitum. Challenge was conducted 31 or 32 days post vaccination with H5N2 highly pathogenic avian Influenza strain.

Serum samples were obtained by bleeding birds from the jugular vein at 15, 30 and days post-vaccination. The serums obtained were stored to 4° C. until running the Hemagglutination Inhibition (HI) test, as described in Example 3, to obtain the antibodies titers.

3. Vaccines and Challenge Virus:

Four different formulations were evaluated independently:
1. Conventional oil emulsion H5HA Mut k+: H5 HA mutk+ antigen was formulated in oil emulsion based (Freund incomplete adjuvant) on Boehringer Ingelheim Vetmedica procedures.
2. Seppic H5HA Mut k+: H5 HA mutk+ antigen formulated with a non conventional adjuvant (ISA 206, W/O/W, from Seppic) based on the recommendation of the supplier.
3. H5HA conventional oil emulsion: H5 HA antigen was formulated in oil emulsion based on Boehringer Ingelheim Vetmedica procedures (Freund Incomplete Adjuvant)
4. Seppic H5HA: H5 HA antigen formulated with a non conventional adjuvant (ISA 206, W/O/W, from Seppic) based on the recommendation of the supplier.

An Avian Influenza Boehringer Ingelheim Vetmedica oil emulsion vaccine was used as control VOLVAC® AI (Boehringer Ingelheim Vetmedica, Mexico).

Challenge were conducted in vaccinated and non vaccinated chickens by inoculation by intra-nasal route with 0.2 ml containing $10^{6.7}$ CEID per bird of the H5N2 challenge virus. After the challenge, signs and mortality were recorded. Ten days post-inoculation all the survivors chickens were euthanized according to animal lab. procedures 4. Results:

Results are described in the following tables:

| Formulation | Vaccination 1 day old Challenge 31 days post vaccination | | Vaccination 10 days old Challenge 32 days post vaccination | |
|---|---|---|---|---|
| | # Dead | Mortality % | # Dead | Mortality % |
| Seppic H5HA Mut k+ | 8/25 | 32% | 0/20 | 0% |
| Conventional oil emulsion H5HA Mut k+ | 0/24 | 0% | 0/20 | 0% |
| Seppic H5HA | 17/25 | 68% | 7/19 | 36.8% |
| H5HA conventional oil emulsion | 4/25 | 16% | 2/20 | 10% |
| Volvac AI KV | | | 0/14 | 0% |
| Negative control | 10/10 | 100% | 14/14 | 100% |

| Vaccine Formulation | Vaccination 1 day old (0.5 ml) | | Vaccination 10 days old (0.5 ml) | |
|---|---|---|---|---|
| | HI titers 30 days post vaccination (MG Log2) | % Protection after Challenge | HI titers 30 days post vaccination (MG Log2) | % Protection after Challenge |
| Seppic H5HA Mut k+ | 0.56 | 68 | 2.5 | 100 |
| Conventional oil emulsion H5HA Mut k+ | 2.59 | 100 | 4.3 | 100 |
| Seppic H5HA | 0.18 | 32 | 1.3 | 63.2 |
| H5HA conventional oil emulsion | 0.7 | 84 | 1.6 | 100 |
| Volvac AI KV | — | — | 8.8 | 100 |
| Negative control | — | — | 0 | 0 |

Positive serum titer is considered $\log_2 4$ according to OIE standards. Based on this criterion serological results were negative but some positive values were observed when compared with the base line. The best serological titers are observed in the vaccine formulated with oil adjuvant and with the H5HA Mut k+ antigen, in birds vaccinated at 1 day of age or 10 days of age. The lowest serological titers were observed in the prototype formulated with Seppic and the H5HA antigen. In the challenge study it was observed, that vaccines prototypes confer protection, particularly with the conventional oil emulsion vaccine formulated with the H5HA Mut k+ antigen. The lowest protection in the challenge study was observed with the Seppic H5HA with 68% of mortality. In contrast, the highest serological titer were observed in birds vaccinated at 10 days compared with birds vaccinated at one day old.

We claim:

1. An isolated H5 protein of influenza virus, wherein said isolated H5 protein comprises the amino acid sequence of SEQ ID NO:4 and includes amino acid 223N, modification 328K+, and amino acid 94N, wherein numbering of the amino acid positions refers to the amino acid position as exemplarily given in SEQ ID NO:1 and wherein the modification 328K+ means that a second Lysine (K+) is inserted at amino acid position 328 of said H5 protein.

2. An isolated H5 protein of influenza virus, said isolated H5 protein having the amino acid 223N, and the modification 328K+, and comprises the amino acid sequence of SEQ ID NO:4, wherein numbering of the amino acid positions of the isolated H5 protein refers to the amino acid position as exemplarily given in SEQ ID NO:1 and wherein the modification 328K+ means that a second Lysine (K+) is inserted at amino acid position 328 of said isolated H5 protein.

3. The isolated H5 protein according to claim 2, wherein said isolated H5 protein has the amino acid 94N.

4. The isolated H5 protein according to claim 2, wherein said isolated H5 protein has the amino acid 120N.

5. The isolated H5 protein according to claim 2, wherein said isolated H5 protein has the amino acid 155N.

6. An immunogenic composition comprising
  a. the isolated H5 protein according to claim 2, and
  b. a pharmaceutical acceptable carrier and/or excipient.

7. The immunogenic composition according to claim 6, wherein said excipient is one or more adjuvants.

8. The immunogenic composition according to claim 7, wherein said adjuvant is an an emulsified oil in water based adjuvant with an immunostimulant.

9. The immunogenic composition according to claim 6, wherein said immunogenic composition comprises one or more further antigens.

10. The immunogenic composition according to claim 9, wherein said further antigen is an antigen of a poultry or mammalian pathogen.

11. The immunogenic composition according to claim 9, wherein said further antigen is H3, H7, or H9 of influenza virus.

12. A kit of parts comprising:
  a. the isolated H5 protein according to claim 2; and
  b. a package leaflet indicating the use of such isolated H5 protein of a) for the treatment or prophylaxis of infections caused by influenza virus.

13. The kit according to claim 12, wherein said kit comprises at least one further antigen of poultry or mammalian pathogen.

\* \* \* \* \*